United States Patent [19]

Sugita et al.

[11] Patent Number: 5,480,982
[45] Date of Patent: Jan. 2, 1996

[54] CRYSTALLINE POTASSIUM SALT OF THIONICOTINAMIDE ADENINE DINUCLEOTIDE PHOSPHATE

[75] Inventors: Kouji Sugita, Osakafu; Tetsuo Kitahara, Osaka; Masatsugu Nonobe, Hyogo; Tsuyosi Fujita, Osaka, all of Japan

[73] Assignee: Oriental Yeast Company, Ltd., Tokyo, Japan

[21] Appl. No.: 945,989

[22] PCT Filed: Mar. 5, 1992

[86] PCT No.: PCT/JP92/00260

§ 371 Date: Nov. 5, 1992

§ 102(e) Date: Nov. 5, 1992

[87] PCT Pub. No.: WO92/15527

PCT Pub. Date: Sep. 17, 1992

[30] Foreign Application Priority Data

Mar. 5, 1991 [JP] Japan ................... 3-123182

[51] Int. Cl.[6] .................................................. C07H 21/02
[52] U.S. Cl. .................................. 536/26.24; 536/26.8
[58] Field of Search ............................................. 536/26.24

[56] References Cited

U.S. PATENT DOCUMENTS 4,151,349   4/1979   Traeger et al. ..................... 536/26.24

FOREIGN PATENT DOCUMENTS 47-14919   5/1972   Japan ..................... 536/26.24

OTHER PUBLICATIONS

*Fluka Catalog, Chemika–BioChemika,* Fluka Chemie AG, Buchs, Switzerland, 1993, p. 1270.

Abraham Stein et al, "The Thionicotinamide Analogs of DPN and TPN. I. Preparation and Analysis," *Biochemistry*, vol. 2, No. 5, pp. 1015–1017, Sep.–Oct. 1963.

*Primary Examiner*—John W. Rollins
*Assistant Examiner*—L. Eric Crane
*Attorney, Agent, or Firm*—Browdy and Neimark

[57] ABSTRACT

The present invention relates to a novel crystalline thio-NADP potassium salt, which is produced by preparing thionicotinamide adenine dinucleotide phosphate (thio-NADP) into the potassium salt thereof and thereafter crystallizing the salt. Conventionally known non-crystalline thio-NADP sodium salt has a strong hygroscopic property to deliquesce on contact with air, of which the storage is therefore difficult. The crystalline thio-NADP potassium salt of the present invention has no hygroscopic property so that it does not deliquesce on contact with air, which can be used as research reagents, diagnostic agents and the like for a long period of time and which can be stored for a long period of time.

1 Claim, No Drawings

CRYSTALLINE POTASSIUM SALT OF THIONICOTINAMIDE ADENINE DINUCLEOTIDE PHOSPHATE

FIELD OF THE INVENTION

The present invention relates to a crystalline potassium salt of thionicotinamide adenine dinucleotide phosphate (referred to as thio-NADP.K salt hereinafter) and the method for producing the same.

Conventionally known non-crystalline thio-NADP.Na salt (referred to as thio-NADP.Na salt hereinafter) shows distinctive hygroscopic property enough to deliquesce on contact with air, so that the storage thereof has been very difficult.

Because the thio-NADP.K salt in accordance with the present invention has no hygroscopic property to deliquesce on contact with air, the salt is extremely useful for the utilities as research reagents, diagnostic agents and the like.

PRIOR ART

It is generally known that thionicotinamide adenine dinucleotide phosphate (referred to as thio-NADP hereinafter), a product from non-natural origins, has a similar level of the coenzyme activity to that of β-nicotinamide adenine dinucleotide phosphate (referred to as β-NADP) as one of the redox coenzymes in living organisms. Based on the property, the utility thereof as a pharmaceutical agent such as a clinical diagnostic agent is under development, as well as the utility as a research agent for biochemistry and physiology. For the measurement of enzyme activity for clinical diagnostics and the analysis of substrate concentration for enzymatic analysis, thio-NADP is far more advantageous than β-NADP in terms of sensitivity and in that reductive-type thio-NADP is colored. The increase in the purity and stability of thio-NADP is required.

A method for producing thio-NADP has conventionally been known, comprising generating thio-NADP through the catalytic activity of NAD nucleosidase (EC 3.2.2.5) in the presence of thionicotinamide and β-NADP, purifying the thio-NADP on a Dowex column, and recovering the purified thio-NADP as an alcohol precipitate followed by drying in vacuum [Japanese Patent Publication No.47-14919; Biochemistry, 2, 1015–1017 (1963)].

However, the thio-NADP-Na salt thus obtained is amorphous, and shows an enriched hygroscopic property, resulting in the deliquescence thereof on contact with air, so that the salt requires special treatment for storage and transport, for example, air degassing and freezing at $-20°$ to $-30°$ C.

Problems to be Solved by the Invention

Even after crystallization process, the thio-NADP.Na salt described above is amorphous without crystallization and it is very difficult to store such salt because of the distinctive hygroscopic property thereof.

Means for Solving the Problems

The present inventors have made investigations as to how to bring about the long-life shelf stability of thio-NADP. As a result, the inventors have found that thio-NADP can be prepared into the potassium salt thereof prior to the crystallization, whereby the resulting salt can be stored for a long period of time because the salt does not show nearly any hygroscopic property.

The present invention relates to a crystalline thio-NADP.K salt and the method for producing the same. The present invention is the first to crystalize thio-NADP as the potassium salt thereof.

Compared with conventional amorphous products, the crystalline thio-NADP.K salt in accordance with the present invention has many advantages in that it is stable because it is highly pure due to no inclusion of inhibitors and in that it has no hygroscopic property.

In accordance with the present invention, the thio-NADP in the form of free acids or salts is prepared into an aqueous solution of the potassium salt, which is then adjusted to pH 1.5 to 5.0, preferably pH 2.0, followed by addition of a hydrophlic organic solvent until the aqueous thio-NADP.K solution begins to get turbid to subsequently be left to stand under cooling. The crystalline thio-NADP.K salt is separated preferably after the completion of the crystallization thereof. As the hydrophilic organic solvent, preferably methanol is used at 0.15 to 2.0-fold, preferably at 0.3 to 1.0-fold the amount of the thio-NADP.K solution, and the above procedure is effected at a given temperature, preferably at room temperature, until the initiation of the crystallization. So as to effect sufficient crystallization of the thio-NADP.K salt, subsequently, the temperature is preferably lowered to $0°$ to $4°$ C. which is then left to stand for 1 to 30 hours. The aqueous thio-NADP.K solution prior to the crystallization procedure is at a concentration of 2 to 50%, preferably 10 to 20%.

Examples of the hydrophilic organic solvents to be used in the present invention include lower alkanol such as methanol, ethanol, propanol and the like, lower ketone such as acetone, ether such as dioxane and the mixtures thereof.

The period for the crystallization is generally completed 2 to 24 hours after the initiation of the crystallization. The crystallization is promoted via the addition of the seed crystal, resulting in a shorter crystallization period.

The crystalline thio-NADP.K salt obtained by the present invention has characteristic properties such that it is purer without containing any inhibitors, and is more stable and has no hygroscopic property, compared with the amorphous thio-NADP.Na salt produced by a usual precipitation method.

The present invention will now be described in examples.

EXAMPLE 1

Twenty grams of amorphous thio-NADP.Na salt in powder is dissolved in 60 ml of deionized water, which is then passed through a cation exchange resin (Dowex 50) to transform the salt into the free acid type, followed by the adjustment to pH 2.0 with a dilute KOH solution. Powdery potassium chloride is added to the resulting solution, to a final 0.1M concentration as the potassium chloride solution, which is then adjusted of its volume to 100 ml with deionized water. While stirring at room temperature, about 80 ml of methanol is added, so that the solution gets slightly turbid. About 20 minutes later, the crystallization of the thio-NADP.K salt is initiated. To complete the crystallization of the thio-NADP.K salt, the mixture is placed in a refrigerator at $2°$ to $4°$ C. About 18 hours later, the crystalline is filtered under aspiration, followed by washing with small amounts of cooled 75% methanol and 100% methanol, which is then dried in vacuo. The yield of crystalline thio-NADP.K salt was about 17 g.

EXAMPLE 2

After stirring 100 ml of a 10% thio-NADP.K salt solution at room temperature, followed by addition of about 20 ml of acetone, the solution gets turbid. A small amount of the seed crystal is added thereto, followed by stirring. Around 30 minutes later, the crystallization begins. In order to complete the crystallization of the thio-NADP.K salt, the mixed solution is placed in a refrigerator at 0° to 4° C. About 18 hours later, the crystal is filtered under aspiration, followed by washing with small amounts of cooled 75% methanol and 100% methanol, which is then dried in vacuo. The yield of crystalline thio-NADP.K salt was about 8 g.

Effects of the Invention.

In accordance with the present invention, thio-NADP is prepared into a non-hygroscopic product without deliquescence on contact with air, via the preparation of the thio-NADP into the potassium salt thereof followed by crystallization, so that the long-life shelf stability of the thio-NADP is achieved.

What is claimed is:

1. Crystalline potassium salt of thionicotinamide adenine dinucleotide phosphate.

\* \* \* \* \*